(12) United States Patent
Garcon

(10) Patent No.: US 7,357,936 B1
(45) Date of Patent: Apr. 15, 2008

(54) ADJUVANT SYSTEMS AND VACCINES

(75) Inventor: Nathalie Garcon, Rixensart (BE)

(73) Assignee: SmithKline Beecham Biologicals, SA, Rixensart (BE)

( * ) Notice: Subject to any disclaimer, the term of this patent is extended or adjusted under 35 U.S.C. 154(b) by 0 days.

(21) Appl. No.: 09/807,657

(22) PCT Filed: Oct. 8, 1999

(86) PCT No.: PCT/EP99/07764

§ 371 (c)(1),
(2), (4) Date: Apr. 16, 2001

(87) PCT Pub. No.: WO00/23105

PCT Pub. Date: Apr. 27, 2000

(30) Foreign Application Priority Data

| Oct. 16, 1998 | (GB) | ................. | 9822703 |
| Oct. 16, 1998 | (GB) | ................. | 9822709 |
| Oct. 16, 1998 | (GB) | ................. | 9822712 |

(51) Int. Cl.
A61K 45/00 (2006.01)
A61K 47/00 (2006.01)
A61K 39/00 (2006.01)
A61K 39/12 (2006.01)
A61K 39/29 (2006.01)

(52) U.S. Cl. ............... 424/278.1; 424/184.1; 424/282.1; 424/283.1; 424/204.1; 424/226.1; 424/227.1; 514/4

(58) Field of Classification Search ............ 424/283.1, 424/450, 499, 184.1, 188.1, 189.1, 193.1, 424/194.1, 199.1, 201.1, 202.1, 204.1, 208.1, 424/226.1, 229.1, 228.1, 278.1, 282.1, 682, 424/690; 514/4, 8, 54

See application file for complete search history.

(56) References Cited

U.S. PATENT DOCUMENTS

| 5,252,327 | A | * | 10/1993 | Bernhardt | ................. | 424/278.1 |
| 5,698,679 | A | * | 12/1997 | Nemazee | ................. | 530/387.3 |
| 5,733,011 | A | * | 3/1998 | Young et al. | ............ | 297/423.11 |
| 5,750,110 | A | * | 5/1998 | Prieels et al. | ............ | 424/184.1 |
| 5,776,468 | A | * | 7/1998 | Hauser et al. | ............ | 424/192.1 |
| 5,817,314 | A | * | 10/1998 | So et al. | ................. | 424/184.1 |
| 5,972,346 | A |   | 10/1999 | Hauser et al. | | |
| 6,306,404 | B1 | * | 10/2001 | LaPosta et al. | ......... | 424/278.1 |
| 6,544,527 | B1 | * | 4/2003 | Rovinski et al. | ......... | 424/208.1 |
| 6,559,282 | B1 | * | 5/2003 | Wang | ................. | 530/324 |
| 6,602,697 | B1 | * | 8/2003 | Cook, III | .................. | 435/239 |
| 6,692,752 | B1 |   | 2/2004 | Slaoui et al. | | |
| 6,867,033 | B1 | * | 3/2005 | Frazer et al. | .............. | 435/235.1 |
| 6,893,644 | B2 |   | 5/2005 | Garcon | | |
| 6,932,972 | B2 |   | 8/2005 | Stephenne et al. | | |

2004/0126394 A1   7/2004   Wettendorff

FOREIGN PATENT DOCUMENTS

| EP | 00/02920 | 12/1978 |
| EP | 00/08728 | 8/1979 |
| EP | 01/11984 | 12/1983 |
| EP | 0198474 | 4/1986 |
| EP | 0226846AB1 | 11/1986 |
| EP | 0299108AB1 | 7/1987 |
| EP | 0278940 | 1/1988 |
| EP | 0304578 | 6/1988 |
| EP | 0414374 | 7/1990 |
| EP | 0576478 | 3/1992 |
| EP | 0511855 | 4/1992 |
| EP | 0633784 | 3/1993 |
| EP | 0689454 | 3/1994 |
| EP | 0 812 593 | 12/1997 |
| EP | 1231264 | 8/2000 |
| GB | 2220211 | 6/1989 |
| WO | WO 88/09797 | 12/1988 |
| WO | WO 90/01496 | 2/1990 |
| WO | WO 91/14703 | 10/1991 |
| WO | WO 92/16231 | 10/1992 |
| WO | WO 93/10152 | 6/1993 |
| WO | WO 1993/19780 | 10/1993 |
| WO | WO 1996/26741 | 10/1993 |
| WO | WO 93/24148 | 12/1993 |
| WO | WO 96/02555 | 2/1996 |
| WO | WO96/02555 | 2/1996 |
| WO | 96/26741 | 9/1996 |
| WO | WO 96/33739 | 10/1996 |
| WO | WO 96/40290 | 12/1996 |
| WO | 97/00697 | 1/1997 |
| WO | 98/15287 | 4/1998 |
| WO | WO 1994/21292 | 7/1998 |
| WO | WO 99/10375 | 3/1999 |

(Continued)

OTHER PUBLICATIONS

Fries et al., "*Liposomal malaria* vaccine in humans: A safe and potent adjuvant strategy", Proc. Natl. Acad. Sci., vol. 89, pp 358-362 (1992).*

(Continued)

Primary Examiner—Zachariah Lucas
(74) Attorney, Agent, or Firm—Michael M. Conger

(57) ABSTRACT

The present invention provides vaccine and adjuvant formulation comprising an immunostimulant and a metal salt. The immunostimulant is adsorbed onto a particle of metal salt and the resulting particle is essentially devoid of antigen.

52 Claims, 6 Drawing Sheets

FOREIGN PATENT DOCUMENTS

| WO | 99/48525 | 9/1999 |
|---|---|---|
| WO | WO 99/45957 | 9/1999 |
| WO | WO 2000/15255 | 3/2000 |
| WO | WO 01/17550 A2 | 3/2001 |
| WO | WO 01/17551 | 3/2001 |
| WO | WO 2003/077942 | 9/2003 |
| WO | WO 2004/056389 | 7/2004 |

OTHER PUBLICATIONS de Swart et al., Journal of Virology, vol. 76 No 22, pp. 11561-11569 (Nov 2002).*
Perbandt et al., JBC Papers in Press, Sep. 12, 2003.*
Wedrychowicz et al., International Journal for Parasitology, vol. 25 No. 9, pp. 1111-1121 (Sep. 1995).*
Mocellin et al., "Cancer vaccine development: on the way to break immune tolerance tomalignant cells," Expermental Cell Research, vol. 299 No. 2, pp. 267-278 (Oct. 2004).*
Rose et al., "Human Papillomavirus Type 11 Recombinant L1 Capsomeres Induce Virus-Neutralizing Antibodies," Journal of Virology, vol. 72 No. 7, pp. 6151-6154 (Jul. 1998).*
Stevenson, Freda K, "Update on cancer vaccines", Current Opinion in Oncology, vol. 17 No. 6, pp. 573-577 (Nov. 2005).*
ImmunEasy Mouse Adjuvant Handbook, Qiagen Worldwide, pp. 1-20. Jun. 2002.
Weeratna, et al., "CpG DNA Induces Stronger Immune Responses with Less Toxicity than Other Adjuvants", Vaccine, 18: 1755 (2000).
Davis, et al., "CpG DNA is a Potent Enhancer of Specific Immunity in Mice Immunized with Recombinant Hepatitis B Surface Antigen", J. Immunology, 160: 870 (1998). (Published Erratum appears in J. Immunology, 162: 3103 (1999).
Lipford, et al., "CpG-Containing Synthetic Oligonucleotides Promote B and Cytotoxic T Cell Responses to Protein Antigen: A New Class of Vaccine Adjuvants", Eur. J. Immunol., 27: 2340 (1997).
Krieg, et al., "CpG Motifs in Bacterial DNA Trigger Direct B-Cell Activation", Nature, 374: 546 (1995).
U.S. Appl. No. 10/070,479, filed Jun. 26, 2002.
Van de Eynde, et al., "Tumor Antigens Recognized by T Lymphocytes," Int J. Clin Res, 1997 27:81-86.
Correale, et al., "In Vitro Generation of Human Cytotoxic T Lymphocytes Specific for Peptides Derived from Prostate-Specific Antigen," Journal of the National Cancer Institute, 1997 89:293-300.
Robbins, et al., "Human Tumor Antigens Recognized by T Cells," Current Opinion in Immunology, 1996 8:628-636.
Andre, et al., "Inactivated Candidate Vaccines for Hepatitis A," Melnick JL(ed.): Prog Med Virol, Basel, Karger, 1990 37:72-95.
Eddleston, "Modern Vaccines," The Lancet, 1990 335:1142-1145.
Dalsgaard, "Saponin Adjuvants," Springer-Verlag, 1974 44:243-254.
Tiollais, et al., "The Hepatitis B Virus," Nature, 1985 317:489-495.
Harford, et al., "Expression of Hepatitis B Surface Antigen in Yeast," Develop. Biol. Standard, 1983 54:125-130.
Cregg, et al., "High-Level Expression and Efficient Assembly of Hepatitis B Surface Antigen in the Methylotrophic Yeast, Pichia Pastoris," Biotechnology1987 5:479-485.
Vogel, et al., "A Compendium of Vaccine Adjuvants and Excipients," Vaccine Design- the Subunit and Adjuvant Approach, Plenum Press, 1995 Chapter 7:141-228.
Newman, et al., "Adjuvant Formulation Concerns," Vaccine Design- the Subunit and Adjuvant Approach, Plenum Press, 1995, Chapter 1, 4.6:26-27.
Gupta, et al., "Adjuvant Properties of Aluminum and Calcium Compounds," Vaccine Design- the Subunit and Adjuvant Approach, Plenum Press, 1995, Chapter 8:229-248.
Hem, et al., "Structure and Properties of Aluminum-Containing Adjuvants," Vaccine Design- the Subunit and Adjuvant Approach, Plenum Press, 1995, Chapter 9:249-276.
Ulrich, et al., "Monophosphoryl Lipid A as an Adjuvant: Past Experiences and New Directions," Vaccine Design- the Subunit and Adjuvant Approach, Plenum Press, 1995, Chapter 21:495-524.
Purcell, "Approaches to Immunization against Hepatitis A Virus," Viral Hepatitis and Liver Disease, Williams & Wilkins, 1990, Section 2:41-46.
Day, et al., "Evaluation of the Human B Lymphocyte Response to Hepatitis A Virus," Viral Hepatitis and Liver Disease, Williams & Wilkins, 1990, Section 2:69-71.
Andre, "Development of a Vaccine against Hepatitis A," Viral Hepatitis and Liver Disease, Williams & Wikins, 1990, Section 2:85-87.
Sjogren, et al., "Inactivated Hepatitis A Vaccine in Adults: Comparison of Dose Schedules and Evaluation of Different Preparations," Viral Hepatitis and Liver Disease, Williams & Wilkins, 1990, Section 2:88-90.
Ellerbeck, et al., "Safety and Immunogenicity of an Inactivated Hepatitis A Virus Vaccine," Viral Hepatitis and Liver Disease, Williams & Wilkins, 1990, Section 2:91-93.
Lewis, et al., "Use of a Live, Attenuated Hepatitis A Vaccine to Prepare a Highly Purified, Formalin-inactivated Hepatitis A Vaccine," Viral Hepatitis and Liver Disease, Williams & Wilkins, 1990, Section 2:94-97.
Ambrosch, et al., "Comparison of HA V Antibodies Induced by Vaccination, Passive Immunization, and Natural Infection", Viral Hepatitis and Liver Disease, Williams & Wilkins, 1990, Section 2:98-100.
Karayiannis, et al., "Vaccination of Tamarins with a Recombinant Vaccinia-Hepatitis A Virus Protects against HAV Infection," Viral Hepatitis and Liver Disease, Williams & Wilkins, 1990, Section 2:101-104.
Weitz, et al., "Empty Hepatitis A Virus Particles in Vaccines," Viral Hepatitis and Liver Disease, Williams & Wilkins, 1990, Section 2:104-108.
Heinricy, et al., "Schedule-dependent Immune Response to Hepatitis A Vaccination," Viral Hepatitis and Liver Disease, Williams & Wilkins, 1990, Section 2:110-111.
Mao, et al., "Further Studies of Attenuated Live Hepatitis A Vaccine (H2 Strain) in Humans," Viral Hepatitis and Liver Disease, Williams & Wilkins, 1990, Section 2:110-111.
Fuchs, et al., "Protection from Infection with Woodchuck Hepatitis Virus (WHV) by Immunization with Recombinant Core Protein of WHV and HGV," Viral Hepatitis and Liver Disease, Williams & Wilkins, 1990, Section 3:267-270.
Margolis, et al., "Immunization Strategies for the Control of Hepatitis A in the United States," Viral Hepatitis and Liver Disease, Williams & Wilkins, 1990, Section 9:724-726.
Mahoney, "Cost of Production of Plasma-derived Hepatitis B Vaccine," Viral Hepatitis and Liver Disease, Williams & Wilkins, 1990, Section 9:730-731.
De Knegt, et al., "Low-Dose Hepatitis B Vaccination with Recombinant Vaccine in Medical Students," Viral Hepatitis and Liver Disease, Williams & Wilkins, 1990, Section 9:741-744.
Lee, et al., "Immunogenicity and Protective Efficacy on Low-Dose Hepatitis B Vaccine in Newborns of HBsAg-Carrier Mothers," Viral Hepatitis and Liver Disease, Williams & Wilkins, 1990, Section 9:744-746.
Yamauchi, et al., "Reduced Immunogenicity of Hepatitis B Vaccine in Patients with Chronic Non-A, Non-B (Type C) Hepatitis," Viral Hepatitis and Liver Disease, Williams & Wilkins, 1990, Section 9:747-748.
Yeoh, et al., "Determinants of Immunogenicity and Efficacy of Hepatitis B Vaccine in Infants," Viral Hepatitis and Liver Disease, Williams & Wilkins, 1990, Section 9:749-752.
Leslie, et al., "Prevention of the Hepatitis B Virus Carrier State in Infants of Mothers with High and Low Serum Levels of HBV-DNA," Viral Hepatitis and Liver Disease, Williams & Wilkins, 1990, Section 9:753-456.
Boxall, et al., "HBV-DNA Levels in Hepatitis B Carrier Mothers; Relationship with Protection against Parinatal Transmission by Vaccine," Viral Hepatitis and Liver Disease, Williams & Wilkins, 1990, Section 9:757-759.

Hwang, et al., "Five-year Follow-up of HBV Vaccination with Plasma-derived Vaccine in Neonates: Evaluation fo Immunogenicity and Efficacy against Perinatal Transmission," *Viral Hepatitis and Liver Disease*, Williams & Wilkins, 1990, Section 9:759-761.

Wainwright, et al., "Duration of Immunogenicity and Efficacy of Hepatitis B Vaccine in a Yupik Eskomo Population-Preliminary Results of an 8-Year Study," *Viral Hepatitis and Liver Disease*, Williams & Wilkins, 1990, Section 9:762-766.

Hadler, et al., "Evaluation of Long-Term Protection by Hepatitis B Vaccine for Seven to Nine Yers in Homosexual Men," *Viral Hepatitis and Liver Disease*, Williams & Wilkins, 1990, Section 9:766-768.

Milich, et al., "Importance of Subtype in the Immune Response to the PreS2 Region," *Viral Hepatitis and Liver Disease* Williams & Wilkins, 1990, Section 9:768-773.

Hattum, et al., "In Vitro Anti-HBs Production by Individual B Cells of Responders to Hepatitis Vaccine Who Subsequently Lost Antibody," *Viral Hepatitis and Liver Disease*, Williams & Wilkins, 1990, Section 9:774-776.

Lee, et al., "The Second Booster for the Proviously Hepatitis B Vaccine-immunized High-Risk Children," *Viral Hepatitis and Liver Disease*, Williams & Wilins, 1990, Section 9:776-778.

Takahashi, et al., "Identification of Low-Level Hepatitis B Viral Genome in Hepatitis B Vaccine Nonresponders in Japan," *Viral Hepatitis and Liver Disease*, Williams & Wilkins, 1990, Section 9:779-781.

Sciariada, et al., "Immune Response to Hepatitis B Vaccine in Persons with Anti-HBc Alone," *Viral Hepatitis and Liver Disease*, Williams & Wilkins, 1990, Section 9:782-784.

Schödel, et al., "Oral Immunization of Mice with Hepatitis B Virus B Cell and T Cell Epitopes Expressed in Salmonella Vaccine Strains," *Viral Hepatitis and Liver Disease*, Williams & Wilkins, 1990, Section 9:784-787.

Fay, et al., "Strategies for Implementing Successful Hepatitis B Vaccination Programs," *Viral Hepatitis and Liver Disease*, Williams & Wilkins, 1990, Section 10:831-833.

Milich, "A Synthetic PreS2 Immunogen," *Viral Hepatitis and Liver Disease*, Williams & Wilkins, 1990, Section 10:840-844.

Michel, et al., "Hepatitis B Virus Surface Antigen (HBsAg) as Carrier for Foreign Antigenic Determinants," *Viral Hepatitis and Liver Disease*, Williams & Wilkins, 1990, Section 10:844-846.

Robinson, et al., "Hepatitis B Virus Antigens Expressed by Live Salmonella Vaccine Strains Elicit Humoral and Cellular Immune Responses in Mice," *Viral Hepatitis and Liver Disease*, Williams & Wilkins, 1990, Section 10:847-849.

Tong, et al., "Immunoprophylaxis of Neonates against Hepatitis B," *Viral Hepatitis and Liver Disease*, Williams & Wilkins, 1990, Section 10:849-855.

Grob, et al., "Unresolved Issues in Hepatitis B Immunization," *Viral Hepatitis and Liver Disease*, Williams & Wilkins, 1990, Section 10:856-860.

U.S. Appl. No. 10/540,099, filed Dec. 18, 2003, Dubin et al.
U.S. Appl. No. 10/508,222, filed Mar. 17, 2003, Wettendorff, et al.
U.S. Appl. No. 10/070,479, filed Sep. 07, 2000, Wettendorff, et al.
U.S. Appl. No. 08/809,643, filed Feb. 15, 1996 Garcon et al.
U.S. Appl. No. 10/465,763, filed Jun. 19, 2003, Garcon et al.
U.S. Appl. No. 08/525,638, filed Mar. 14, 1994, Hauser et al.
U.S. Appl. No. 09/661,926, filed Sep. 14, 2000, Slaoui et al.
U.S. Appl. No. 09/730,930, filed Dec. 6, 2000, Claude et al.
U.S. Appl. No. 09/405,469, filed Sep. 24, 1999, Garcon et al.
U.S. Appl. No. 10/760,938, filed Jan. 20, 2004, Slaoui et al.
U.S. Appl. No. 11/158,652, filed Jun. 22, 2005, Slaoui et al.
U.S. Appl. No. 09/646,205, filed Oct. 27, 2000, Slaoui et al.
U.S. Appl. No. 08/307,668, filed Sep. 29, 1994, Garcon et al.
U.S. Appl. No. 08/440,872, filed May 15, 1995, Garcon et al.

* cited by examiner

Figure 1 shows anti-HBs Ig antibody responses measured on individual sera and represented as GMT.
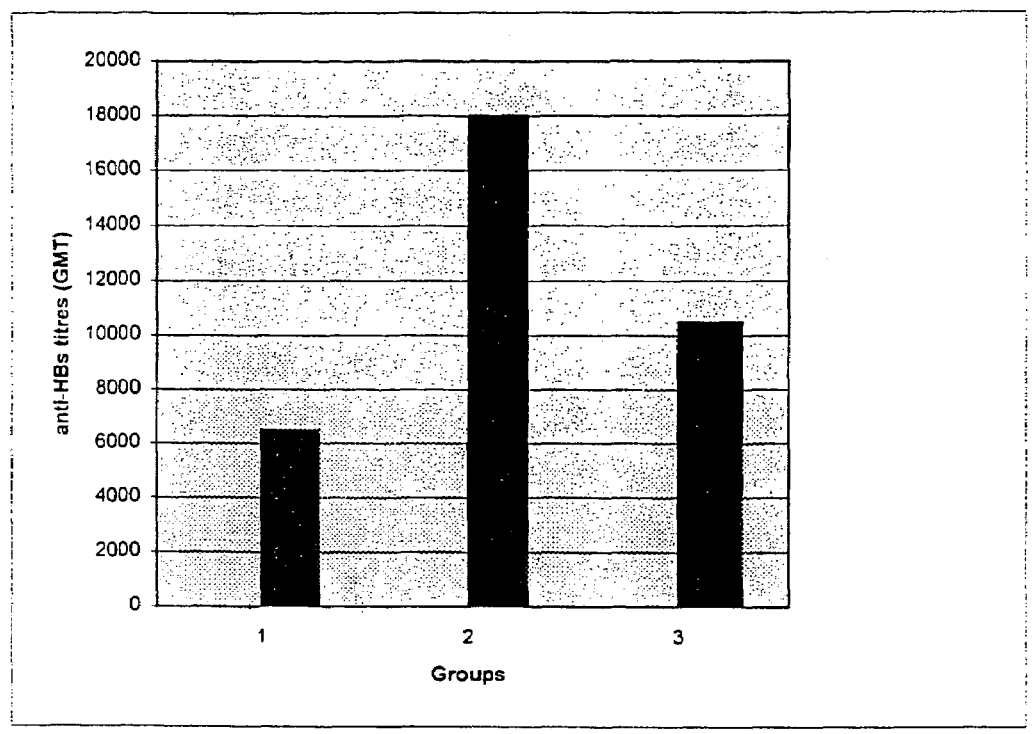
| Group | ELISA Titres (GMT) |
|---|---|
| 1 | 6495 |
| 2 | 18006 |
| 3 | 10496 |

Figure 2 shows the isotypic repartition (IgG1, IgG2a and IgG2b) calculated from analysis on pooled sera .
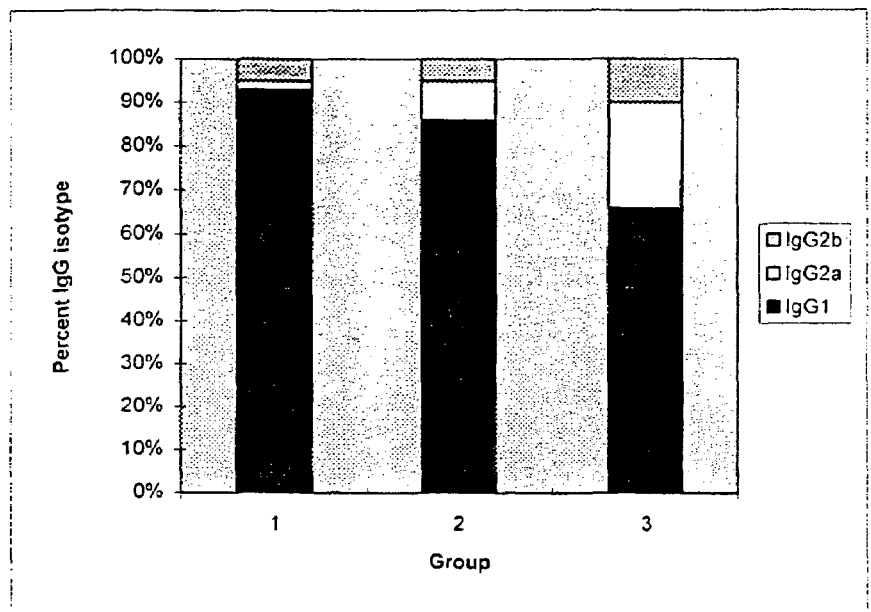
| Group | IgG1 % | IgG2a % | IgG2b % |
|---|---|---|---|
| 1 | 93 | 2 | 5 |
| 2 | 86 | 9 | 5 |
| 3 | 66 | 24 | 10 |

Figure 3, shows the lymphoproliferation monitored in splenic cells restimulated with HBs.
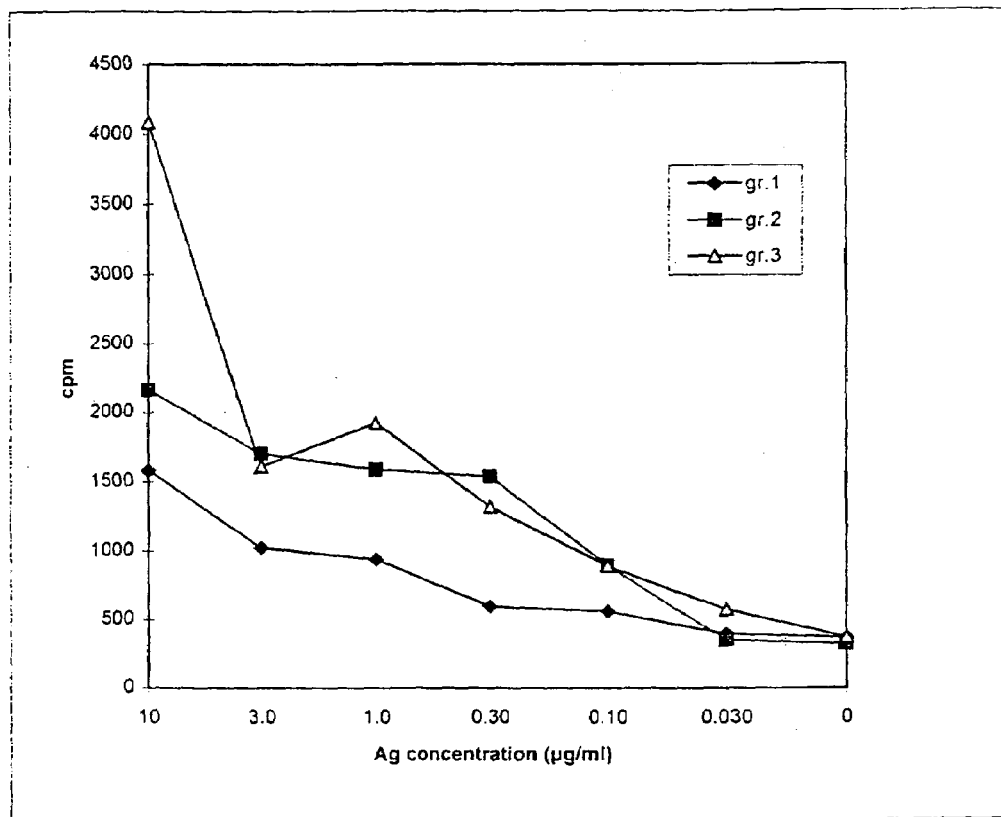

Figure 4 shows the cytokine production monitored in splenic cells restimulated with HBs.
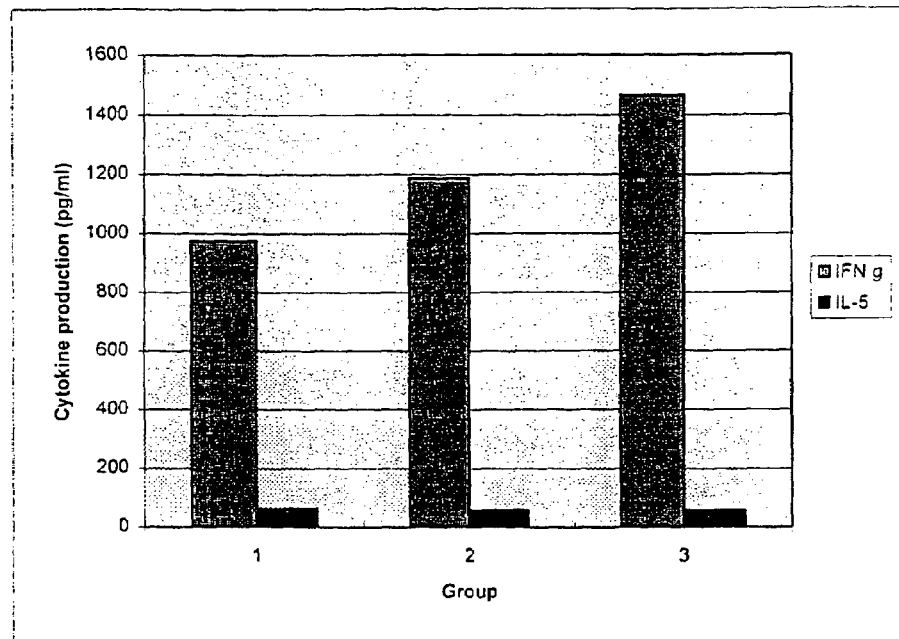
| Cytokine (pg/ml) | | Gp 1 | Gp 2 | Gp 3 |
|---|---|---|---|---|
| IFN g | HBsAg 10μg/ml | 975 | 1187 | 1465 |
| | Blank | 157* | 173* | 173* |
| IL-5 | HBsAg 10μg/ml | 64* | 59* | 59* |
| | Blank | 64* | 59* | 59* |
| RATIO IFNg/IL-5 | | 15.2 | 20.1 | 24.8 |
* = limit of quantification Figure 5, Anti HSV gD titres (see example 3).
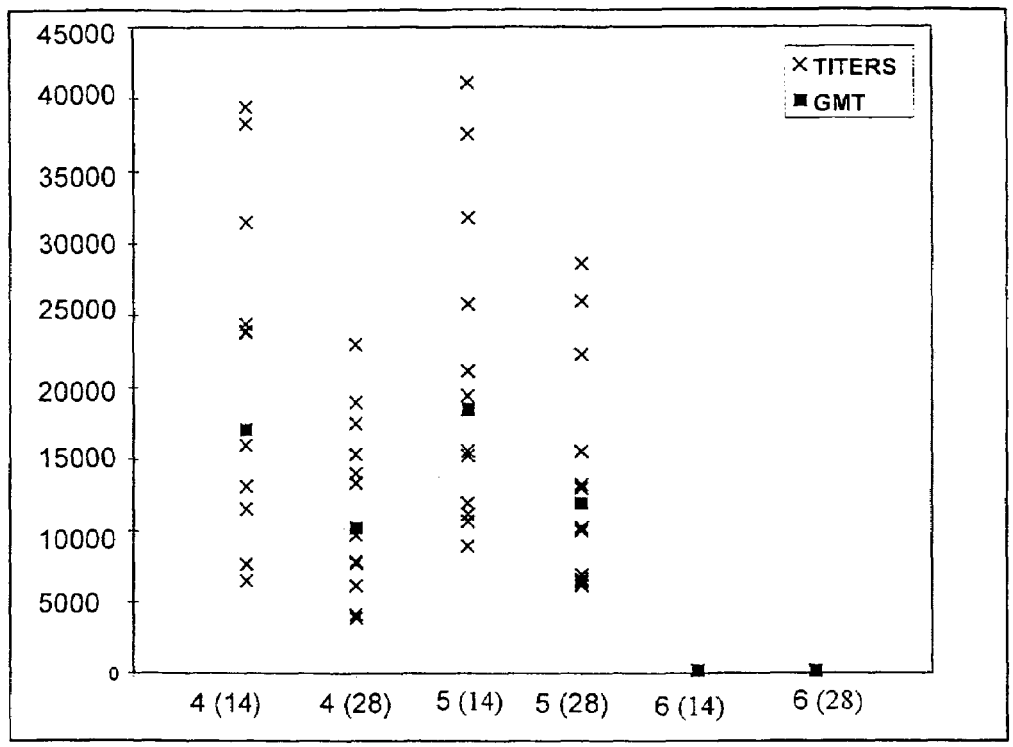
| Group (Bleeding schedule) | ELISA titres | |
|---|---|---|
| | GMT | Average |
| 4 (14 days post II) | 17090 | 20336 |
| 4 (28 days post II) | 10227 | 11825 |
| 5 (14 days post II) | 18508 | 20903 |
| 5 (28 days post II) | 11965 | 13796 |
| 6 (14 days post II) | 200 | 200 |
| 6 (28 days post II) | 200 | 200 |

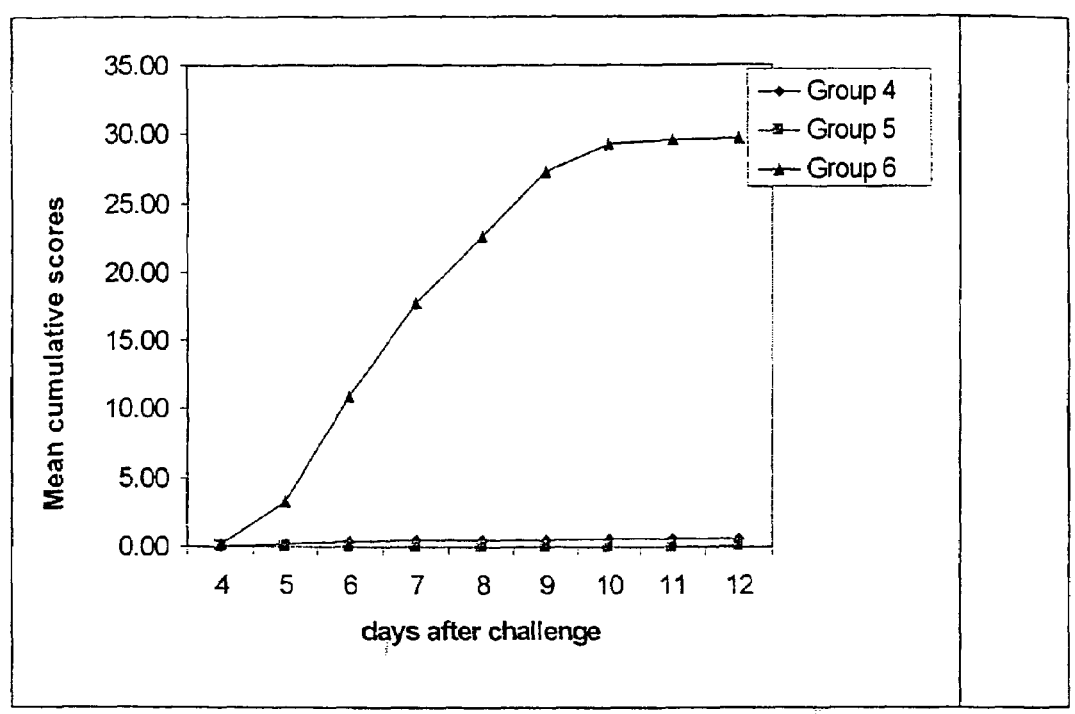
Figure 6, Mean cumulative HSV lesion scores (see example 3)

US 7,357,936 B1

ADJUVANT SYSTEMS AND VACCINES

This is a 371 of International Application PCT/EP99/07764, filed Oct. 8, 1999, which claims benefit from the following Provisional Applications: GB 9822709.3 filed Oct. 16, 1998; GB 9822703.6 filed Oct. 16, 1998; and GB 9822712.7 filed Oct. 16, 1998.

The present invention relates to improved vaccines, adjuvant systems, and processes for the preparation of such vaccines and adjuvant systems. In particular, the vaccines and adjuvant systems of the present invention comprise metallic salts and additional immunostimulants such as monophosphoryl lipid A, or derivatives thereof, Quil A or derivatives thereof, or immunostimulatory oligonucleotides such as CpG.

Aluminium salts are well known in the art as providing a safe excipient with adjuvant activity. The mechanism of action of these adjuvants are thought to include the formation of an antigen depot such that antigen may stay at the site of injection for up to 3 weeks after administration, and also the formation of antigen/metallic salt complexes which are more easily taken up by antigen presenting cells. In addition to aluminium, other metallic salts have been used to adsorb antigens, including salts of zinc, calcium, cerium, chromium, iron, and berilium. The hydroxide and phosphate salts of aluminium are the most common.

Vaccine formulations containing aluminium salts, antigen, and additional immunostimulant are known in the art. Such formulations induced greater immune responses in comparison with those stimulated by aluminium salts and antigen alone. Formulation of these vaccine preparations have previously involved a specific manufacturing procedure, since it was believed that in order for optimal immune responses to occur, the antigen must be adsorbed onto the same aluminium salt particle as the immunostimulant. In this way when antigen is taken up by an antigen presenting cell, the co-adsorbed immunostimulant exerts its stimulatory activity directly onto that same antigen presenting cell.

Aluminium based vaccine formulations wherein the antigen and the immunostimulant 3-de-O-acylated monophosphoryl lipid A (3D-MPL), are adsorbed onto the same particle are described in EP 0 576 478 B1. EP 0 689 454 B1, and EP 0 633 784 B1. In these cases then antigen is first adsorbed onto the aluminium salt followed by the adsorption of the immunostimulant 3D-MPL onto the same aluminium salt particles. Such processes first involve the suspension of 3D-MPL by sonication in a water bath until the particles reach a size of between 80 and 500 nm. The antigen is typically adsorbed onto aluminium salt for one hour at room temperature under agitation. The 3D-MPL suspension is then added to the adsorbed antigen and the formulation is incubated at room temperature for 1 hour, and then kept at 4° C. until use.

The formulation processes of the prior art provide for potent vaccines from an immunological point of view, however, they do contain several commercial disadvantages. In order for a vaccine to be suitable for human administration, the process must be uniform and be subject to Good Manufacturing Practice (GMP) control, and Quality Control (QC). In some cases the processes of the prior art provide a vaccine wherein all of the antigen, or antigens, are adsorbed onto the same particle of metallic salt. The process is then complicated by the requirement for the 3D-MPL to be adsorbed onto the same metallic particle. This may be particularly problematical in the case of combination vaccines containing multiple antigens (whose adsorption may be dependent on the affinity of each antigen to the particular metallic salt at a given pH). The processes of the prior art may have problems, depending on which antigens are present, in reproducibility and vaccine QC. Furthermore, if anything undesired occurs with the QC of one particular antigen, or an occurrence which may result in the contamination of the vaccine, this may result in the waste all of the individual components, and not just the particular antigen in which the problem occurred. Moreover, in some circumstances combination vaccines may require the sequential addition of the antigens, such a process being hugely time consuming and expensive. The processes of the prior art may, therefore, be complex, difficult to control, and expensive.

Surprisingly, the present inventors have discovered that it is not necessary to adsorb antigen and the immunostimulant onto the same particle. In contrast to the accepted thinking in the art, it has been found that good vaccines may be produced when antigen is adsorbed onto particular metallic salt particles which are discrete from those metallic salt particles which are associated with the immunostimulant.

The improved process comprises the absorption of immunostimulant, onto a metallic salt particle, followed by the absorption of the antigen onto another metallic salt particle, followed by the mixing of the discrete metallic particles to form a vaccine. The present invention also provides for an adjuvant composition an immunostimulant, absorbed onto a metallic salt particle, characterised in that the metallic salt particle is substantially free of other antigen. Furthermore, vaccines are provided by the present invention and are characterised in that the immunostimulant is absorbed onto particles of metallic salt which are substantially free from other antigen, and in that the particles of metallic salt which are absorbed to the antigen are substantially from of other immunostimulant. An immunostimulant may include, but is not limited to, monophosphoryl lipid A or a derivative thereof. Thus, vaccines are provided comprising two major populations of complexes a first complex comprising (a) an immunostimulant adsorbed onto a metallic salt particle characterised in that said metallic salt particle is substantially free of antigen; and a second complex comprising (b) antigen adsorbed onto a metallic salt particle characterised in that said metallic salt particle is substantially free of the immunostimulant of the first complex.

Accordingly, the present invention provides an adjuvant formulation comprising immunostimulant Which has been adsorbed onto a particle of a metallic salt, characterised in the composition is substantially free of other antigen. Moreover, this adjuvant formulation is an intermediate which is required during the process of the present invention, for the manufacture of a vaccine. Accordingly there is provided a process for the manufacture of a vaccine comprising admixing the adjuvant composition of the invention with an antigen. Preferably, the antigen has been pre-adsorbed onto a metallic salt. Said metallic salt may be identical or similar to the metallic salt which is adsorbed onto the immunostimulant.

The present invention further provides for a vaccine composition comprising immunostimulant adsorbed onto a first particle of a metallic salt, and antigen adsorbed onto a metallic salt, characterised in that first and second particles of metallic salt are different.

Alternatively, vaccines which form part of the present invention comprise two major populations of complexes, a first complex comprising (a) immunostimulant adsorbed onto a metallic salt particle, characterised in that said metallic salt particle is substantially free of antigen: and a second complex comprising (b) antigen adsorbed onto a metallic salt particle. Also the vaccine composition can comprising two major populations of complexes, a first complex comprising (a) immunostimulant adsorbed onto a metallic salt particle, characterising in that said metallic salt particle is substantially free of antigen; and a second complex comprising (b) antigen adsorbed onto a metallic salt particle, characterised in that said metallic salt-particle is substantially free of immunostimulant.

The metallic salts present in these two major populations of complexes may be identical or different. Furthermore, in the case of a combination vaccine, wherein a plurality of different antigens may be present, the second complex (described above) may comprise a plurality of antigens adsorbed onto different metallic particles.

The definition of substantially free of other antigens, in relation to this invention, is where not more than 20% by mass of the total material capable of adsorbing to the particle of metallic salt is an other antigen, preferably not more than 10%, and most preferably not more than 5%. Alternatively, the substantially free of immunostimulant, in relation to this invention, is where not more than 20% by mass of the total material capable of adsorbing to the particle of metallic salt is immunostimulant, preferably not more than 10%, and most preferably not more than 5%. Routine assays, apparent to the man skilled in the art, could be used to determine whether the antigen and immunostimulant, are adsorbed onto different discrete particles, including but not limited to separation of the vaccine into distinct fractions by free flow of the formulation within an electric field, or techniques such as sedimentation rate analysis which are particularly suited to non-particulate antigens, followed by assaying for the immunostimulant or antigen in the fractions.

Also provided in the present invention is a kit comprising one container having immunostimulant adsorbed onto a metallic salt; and a second container having antigen, preferably said antigen being adsorbed onto a metallic salt.

The process of the present invention is especially useful when commercial scale quantities of combination vaccines are required. Combination vaccines are single dose vaccines which contain more than one antigen from more than one pathogen. Such vaccines may reduce the number of vaccinations required to induce protection against many pathogens and diseases.

For example, if a vaccine comprises $AlOH_3$, 3D-MPL, and the antigens V, W, X, Y, Z, previous processes involve formulating the antigens and the 3D-MPL onto the same particle of $AlOH_3$. Such prior art processes require that V, W, X, Y, Z are adsorbed onto the AlOH, followed by the addition of free 3D-MPL onto each of the pre-adsorbed antigen complexes.

In contrast, the formulation process of the present invention antigens V, W, X, Y, Z are each individually adsorbed onto separate particles of $AlOH_3$ in separate containers. 3D-MPL is also adsorbed onto $AlOH_3$ in another container. The vaccine is then formed by the simple admixing of material taken from each of the separate containers. In this case the particles of $AlOH_3$ which is associated with the 3D-MPL may be discrete from the particles of $AlOH_3$ which are associated with the antigens.

Alternatively, the present invention provides a process of making a vaccine comprising an immunostimulant, antigen and a metallic salt, comprising:
1. Adsorbing antigen to a first particle of metallic salt.
2. Adsorbing the immunostimulant to a second particle of a metallic salt, and
3. admixing the products of steps 1 and 2 above.

The present invention provides for a process for the manufacture of vaccines which overcome the problems present in the prior art. Each individual antigen-metallic salt complex may be subject to GMP controls, and should any untoward contamination of a particular antigen-metallic salt preparation then the integrity of other antigens and immunostimulant adjuvant will not be compromised. Surprisingly, and in contrast to the accepted thinking in the art, vaccines produced by the process of the present invention are as potent as those prepared using the process of the prior art.

The definition of immunostimulant within the meaning of this invention can be described as a natural or synthetic compound which has known adjuvant activity, which adjuvant activity derives from the direct or indirect stimulatory effect of the compound upon the cells of the immune system itself and not through other non-stimulatory effects such as a depot effect or targeting to the immune system. Examples of such immunostimulants are described in a chapter in "Vaccine Design—the subunit and adjuvant approach" (Edited by Powell, M. F. and Newman, M. J.; 1995, Pharmaceutical Biotechnology (Plenum Press, New York and London, ISBN 0-306-44867-X) entitled "Compendium of vaccine adjuvants and excipients" by Powell, M. F. and Newman M. These immunostimulants include which are within the present invention include: bacterially derived compounds, like Monophosphoryl lipid A or derivatives thereof: plant derived saponins or derivatives thereof, for example Quil A, or immunostimulatory oligonucleotides such as CpG, block copolymer, cholera toxin, immunostimulatory cytokines such as GM-CSF and IL-1, polyriboA and polyriboU, and Muramyl tripeptide (MTP).

Monophosphoryl lipid A is a bacterially derived compound with adjuvant activity, and is a prefered immunostimulant for use in the present invention. This toxic compound has been altered to form less toxic derivatives, one such derivative is 3 De-O-acylated monophosphoryl lipid A (termed 3D-MPL or d3-MPL, to indicate that position 3 of the reducing end glucosamine is de-O-acylated). For preparation of 3D-MPL, see GB 2 220 211 A. Chemically it is a mixture of 3-deacylated monophosphoryl lipid A with 3, 4, 5 or 6 acylated chains. Preferably in the compositions of the present invention small particle MPL is used. Small particle MPL has a particle size such that it may be sterile-filtered through a 0.22 µm filter. Such preparations are described in International Patent Application No. WO 94/21292. Further improvements are described in GB 9807933.8 which discloses stable preparations of 3D-MPL consisting of the tri and tetra acyl congeners.

GB 2 220 211A mentions that the endotoxicity of the previously used enterobacterial lipopolysaccharides (LPS) is reduced while the immunogenic properties are conserved. However GB 2 220 211 cited these findings merely in connection with bacterial (Gram negative) systems.

Another prefered immunostimulant for use in the present invention is Quil A and its derivatives. Quil A is a saponin preparation isolated from the South American tree *Quilaja Saponaria Molina* and was first described by Dalsgaard et al. in 1974 ("Saponin adjuvants", Archiv. für die gesamte Virusforschung, Vol. 44, Springer Verlag, Berlin, p243–254) to have adjuvant activity. Purified fragments of Quil A have been isolated by HPLC which retain adjuvant activity without the toxicity associated with Quil A (EP 0 362 278), for example QS7 and QS21 (also known as QA7 and QA21). Particular formulations of QS21 have been described which are particularly preferred, these formulations further comprise a sterol (WO96/33739).

CpG is an immunostimulatory oligonucleotide with known adjuvant properties (WO 96/02555). The CpG sequences preferred within the context of this invention are: (TCC ATG AGC TTC CTG ACG TT, Krieg 1826)SEQ ID NO 1, (TCT CCC AGC GTG CGC CAT, Krieg 1758) SEQ ID NO 2, TCG TCG TTT TGT CGT TTT GTC GTT SEQ IN NO 3.

The present invention relates to the particular formulation process and characteristics of the adjuvant. and thus can be utilised with a wide variety of antigens. The vaccines of the present invention can be used for priming and boosting doses, and used for the induction of immune responses to, and protection from infection mediated by, a wide variety of antigens. Also the present invention provides for a method of eliciting an immune response to an antigen comprising the use of a vaccine comprising a metallic salt, immunostimulant, and antigen, wherein the immunostimulant is adsorbed onto particles of metallic salt which are descrete from those metallic salt particles which are adsorbed to the antigen. Some of the pathogens and antigens are listed below.

Viral hepatitis, caused by the A, B, C, D, and E hepatitis viruses, is a very common viral illness. Via the B and C viruses, in particular, it is also responsible for many cases of liver cancer. Thus the development of effective vaccines is critical and, despite notable successes, is still an on-going task. A review on modern hepatitis vaccines, including a number of key references, may be found in the Lancet, May 12, 1990 at page 1142 ff (Prof A. L. W. F. Eddleston). See also 'Viral Hepatitis and Liver Disease' (Vyas, B. N., Dienstag, J. L., and Hoofnagle, J. H., eds, Grune and Stratton. Inc. (1984) and 'Viral Hepatitis and Liver Disease' (Proceedings of the 1990 International Symposium, eds F. B. Hollinger. S. M. Lemon and H. Margolis, published by Williams and Wilkins).

As used herein the expression 'hepatitis B antigen' is used to refer to any antigenic material derived from a hepatitis B virus which may be used to induce immunity to the virus in humans.

Infection with hepatitis B virus (HBV) is a widespread problem but vaccines which can be used for mass immunisation are now available, for example the product 'Engerix-B' (SmithKline Beecham plc) which is obtained by genetic engineering techniques.

The preparation of Hepatitis B surface antigen (HBsAg) is well documented. See, for example, Harford et al in Develop. Biol. Standard 54, page 125 (1983), Gregg et al in Biotechnology. 5. page 479 (1987), EP-A-0 226 846. EP-A-0 299 108 and references therein.

As used herein the expression 'Hepatitis B surface antigen' or 'HBsAg' includes any HBsAg antigen or fragment thereof displaying the antigenicity of HBV surface antigen. It will be understood that in addition to the 226 amino acid sequence of the HBsAg S antigen (see Tiollais et al, Nature, 317, 489 (1985) and references therein) HBsAg as herein described may, if desired, contain all or part of a pre-S sequence as described in the above references and in EP-A-0 278 940. In particular the HBsAg may comprise a polypeptide comprising an amino acid sequence comprising residues 12–52 followed by residues 133–145 followed by residues 175–400 of the L-protein of HBsAg relative to the open reading frame on a Hepatitis B virus of ad serotype (this polypeptide is referred to as L*; see EP 0 414 374). HBsAg within the scope of the invention may also include the preS1-preS2-S polypeptide described in EP 0 198 474 (Endotronics) or analogues thereof such as those described in EP 0 304 578 (Mc Cormick and Jones). HBsAg as herein described can also refer to mutants, for example the 'escape mutant' described in WO 91/14703 or European Patent Application Publication Number 0 511 855 Al, especially HBsAg wherein the amino acid substitution at position 145 is to arginine from glycine.

Normally the HBsAg will be in particle form. The particles may comprise for example S protein alone or may be composite particles, for example (L*, S) where L* is as defined above and S denotes the S-protein of HBsAg. The said particle is advantageously in the form in which it is expressed in yeast.

The component affording protection against Hepatitis A is preferably the product known as 'Havrix' (SmithKline Beecham Biologicals) which is a killed attenuated vaccine derived from the HM-175 strain of HAV [see 'Inactivated Candidiate Vaccines for Hepatitis A' by F. E. Andre, A. Hepburn and E. D'Hondt (1980), Prog. Med. Virol. Vol 37, pages 72–95 and the product monograph 'Havrix' published by SmithKline Beecham Biologicals (1991).

Thus, in a preferred embodiment of the present invention a combination vaccine comprising HBsAg and Hepatitis A antigen is provided. Also, provided by the present invention is a process for the production of a hepatitis A and B combination vaccine, and a product derived from that process.

Other combination vaccines are available on the market including the Infanrix™ range, made by SmithKline Beecham Biologicals. Such vaccines are based on a "core" combination of Diptheria toxin, Tetanus toxin, and *B. pertussis* antigens. This vaccine comprises a pertussis component (either killed whole cell *B. pertussis* or accellular *pertussis* which typically consists of two antigens—PT and FHA, and often 69 kDa, optionally with one or both agglutinogen 2 or agglutinogen 3). Such vaccines are often referred to as DTPw (whole cell) or DTPa (acellular).

Particular combination vaccines within the scope of the invention include:
  Diptheria-Tetanus-Pertussis-Hepatitis B (DTP-HB)
  Diptheria-Tetanus-Hepatitis B (DT-HB)
  *Haemophilus influenzae* Type B ("HiB")—Hepatitis B
  DTP-Hib-Hepatitis B
  IPV (inactivated polio vaccine)-DTP-Hib-Hepatitis B The pertussis component is suitably a whole cell pertussis vaccine or an acellular pertussis vaccine containing partially or highly purified antigens. The above combinations may optionally include a component which is protective against Hepatitis A. Preferably the Hepatitis A component is formalin HM-175 inactivated. Advantageously, the HM-175 is purified by treating the cultured HM-175 with trypsin, separating the intact virus from small protease digested protein by permeation chromatography and inactivating with formalin. Advantageously the Hepatitis B combination vaccine is a paediatric vaccine.

Other combination vaccines of the present invention are disclosed in GB 9805105.5 (SmithKline Beecham Biologicals s.a.), such combination vaccines being specially beneficial for vaccines for adolescents. Prefered combinations are based around a "core" combination of a Hepatitis B antigen (Hep B) and a Herpes Simplex (HSV) antigen. Optionally, to this "core" may be added one or more antigens derived from the following group: Epstein Barr Virus (EBV) antigen, Hepatitis A antigen (Hep A). Human Papilloma Virus (HPV) antigen. These combination vaccines may additionally comprise Varicella Zoster Virus (VZV), Human Cytomegalovirus (HCMV) or *toxoplasma* antigens.

Preferably the vaccine formulations of the present invention contain an antigen or antigenic composition capable of eliciting an immune response against a human pathogen, which antigen or antigenic composition is derived from HIV-1, (such as tat, nef, gp120 or gp160), human herpes viruses, such as gD or derivatives thereof or Immediate Early protein such as ICP27 from HSV1 or HSV2, cytomegalovirus ((esp Human)(such as gB or derivatives thereof), Rotavirus (including live-attenuated viruses), Epstein Barr virus (such as gp350 or derivatives thereof), Varicella Zoster Virus (such as gpI, II and IE63), or from a hepatitis virus such as hepatitis B virus (for example Hepatitis B Surface antigen or a derivative thereof), hepatitis A virus, hepatitis C virus and hepatitis E virus, or from other viral pathogens, such as paramvxoviruses: Respiratory Syncytial virus (such as F and G proteins or derivatives thereof), parainfluenza virus, measles virus, mumps virus, human papilloma viruses (for example HPV6, 11, 16, and 18), flaviviruses (e.g. Yellow Fever Virus, Dengue Virus, Tick-borne encephalitis virus, Japanese Encephalitis Virus) or Influenza virus, or derived from bacterial pathogens such as *Neisseria* spp, including *N. gonorrhea* and *N. meningitidis* (for example capsular polysaccharides and conjugates thereof, transferrin-binding proteins, lactoferrin binding proteins, PilC, adhesins); *Streptococcus* spp, including *S. pneumoniae* (for example capsular polysaccharides and conjugates thereof, PsaA, PspA, streptolysin, choline-binding proteins), *S. pyogenes* (for example M proteins or fragments thereof, C5A protease, lipoteichoic acids), *S. agalactiae, S. mutans; Haemophilus* spp, including *H. influenzae* type B (for example PRP and conjugates thereof), non typeable *H. influenzae* (for example OMP26, high molecular weight adhesins, P5, P6, lipoprotein D), *H. ducreyi; Morarella* spp, including *M catarrhalis*, also known as *Branhamella catarrhalis* (for example high and low molecular weight adhesins and invasins); *Bordetella* spp, including *B. pertussis* (for example pertactin, pertussis toxin or derivatives thereof, filamenteous hemagglutinin, adenylate cyclase, fimbriae), *B. parapertussis* and *B. bronchiseptica; Mycobacterium* spp., including *M. tuberculosis* (for example ESAT6, Antigen 85A, -B or -C), *M. bovis, M. leprae, M. avium, M. paratuberculosis, M. smegmatis; Legionella* spp, including *L. pneumophila; Escherichia* spp, including *enterotoxic E. coli* (for example colonization factors, heat-labile toxin or derivatives thereof, heat-stable toxin or derivatives thereof), enterohemorragic *E. coli*, enteropathogenic *E. coli* (for example shiga toxin-like toxin or derivatives thereof); *Vibrio* spp, including *V. cholera* (for example cholera toxin or derivatives thereof); *Shigella* spp, including *S. sonnei, S. dysenteriae, S. flexnerii; Yersinia* spp, including *Y. enterocolitica* (for example a Yop protein), *Y. pestis, Y. pseudotuberculosis; Campylobacter* spp, including *C. jejuni* (for example toxins, adhesins and invasins) and *C. coli; Salmonella* spp, including *S. typhi, S. paratyphi, S. choleraesuis, S. enteritidis, Listeria* spp., including *L. monocytogenes; Helicobacter* spp, including *H. pylori* (for example urease, catalase, vacuolating toxin); *Pseudomonas* spp, including *P. aeruginosa; Staphylococcus* spp., including *S. aureus, S. epidermidis; Enterococcus* spp., including *E. faecalis, E. faecium; Clostridium* spp., including *C. tetani* (for example tetanus toxin and derivative thereof), *C. botulinum* (for example botulinum toxin and derivative thereof), *C. difficile* (for example *clostridium* toxins A or B and derivatives thereof); *Bacillus* spp., including *B. anthracis* (for example botulinum toxin and derivatives thereof), *Corvnebacterium* spp., including *C. diphtheriae* (for example diphtheria toxin and derivatives thereof); *Borrelia* spp., including *B. burgdorferi* (for example OspA, OspC, DbpA, DbpB), *B. garinii* (for example OspA, OspC, DbpA, DbpB), *B. afzelii* (for example OspA, OspC, DbpA, DbpB), *B. andersonii* (for example OspA, OspC, DbpA, DbpB), *B. hermsii; Ehrlichia* spp., including *E. equi* and the agent of the Human Granulocytic Ehrlichiosis; *Rickettsia* spp, including *R. rickettsii, Chlamydia* spp., including *C. trachomatis* (for example MOMP, heparin-binding proteins), *C. pneumoniae* (for example MOMP, heparin-binding proteins), *C. psittaci; Leptospira* spp., including *L. interrogans; Treponema* spp., including *T. pallidum* (for example the rare outer membrane proteins), *T. denticola, T. hyodysenteriae;* or derived from parasites such as *Plasmodium* spp., including *P. falciparum; Toxoplasma* spp., including *T. gondii* (for example SAG2, SAG3, Tg34); *Entamoeba* spp. including *E. histolytica; Babesia* spp., including *B. microti, Trypanosoma* spp., including *T. cruzi; Giardia* spp., including *G. lamblia; Leshmania* spp., including *L. major, Pneumocystis* spp., including *P. carinii; Triclomonas* spp., including *T. vaginalis, Schisostoma* spp., including *S. mansoni,* or derived from yeast such as *Candida* spp., including *C. albicans; Cryptococcus* spp., including *C. neoformans.*

In one preferred aspect the vaccine formulation of the invention comprises the HIV-1 antigen, gp120, especially when expressed in CHO cells. In a further embodiment, the vaccine formulation of the invention comprises gD2t as hereinabove defined.

In a preferred embodiment of the present invention vaccines containing the claimed adjuvant comprise the HPV viruses considered to be responsible for genital warts, (HPV 6 or HPV 11 and others), and the HPV viruses responsible for cervical cancer (HPV16, HPV18 and others). Particularly preferred forms of vaccine comprise L1 particles or capsomers, and fusion proteins comprising one or more antigens selected from the HPV 6 and HPV 11 proteins E6, E7, L1, and L2. The most preferred forms of fusion protein are: L2E7 as disclosed in GB 95 15478.7, and proteinD(1/3)-E7 disclosed in GB 9717953.5 (WO99/10375).

Vaccines of the present invention further comprise antigens derived from parasites that cause Malaria. For example, preferred antigens from *Plasmodia falciparum* include RTS, S and TRAP. RTS is a hybrid protein comprising substantially all the C-terminal portion of the circumsporozoite (CS) protein of *P. falciparum* linked via four amino acids of the preS2 portion of Hepatitis B surface antigen to the surface (S) antigen of hepatitis B virus. It's full structure is disclosed in the International Patent Application No. PCT/EP92/02591, published under Number WO 93/10152 claiming priority from UK patent application No. 9124390.7. When expressed in yeast RTS is produced as a lipoprotein particle, and when it is co-expressed with the S antigen from HBV it produces a mixed particle known as RTS, S. TRAP antigens are described in the International Patent Application No. PCT/GB89/00895, published under WO 90/01496. A preferred embodiment of the present invention is a Malaria vaccine wherein the antigenic preparation comprises a combination of the RTS, S and TRAP antigens. Other plasmodia antigens that are likely candidates to be components of a multistage Malaria vaccine are *P. faciparum* MSP1, AMA1, MSP3, EBA, GLURP, RAP1, RAP2, Sequestrin, PfEMP1, Pf332, LSA1, LSA3, STARP, SALSA, PfEXP1, Pfs25, Pfs28, PFS27/25, Pfsl6, Pfs48/45, Pfs230 and their analogues in *Plasmodium* spp.

The formulations may also contain an anti-tumour antigen and be useful for the immunotherapeutic treatment of cancers. For example, the adjuvant formulation finds utility with tumour rejection antigens such as those for prostrate, breast, colorectal, lung, pancreatic, renal or melanoma cancers.

Exemplary antigens include MAGE 1 and MAGE 3 or other MAGE antigens for the treatment of melanoma, PRAME, BAGE, or GAGE (Robbins and Kawakami, 1996, Current Opinions in Immunology 8, pps 628–636; Van den Eynde et al., International Journal of Clinical & Laboratory Research (submitted 1997): Correale et al. (1997), Journal of National Cancer Institute 89, p293. Indeed these antigens are expressed in a wide range of tumour types such as melanoma, lung carcinoma, sarcoma and bladder carcinoma. Other Tumor-Specific antigens are suitable for use with adjuvant of the present invention and include, but are not restricted to Prostate specific antigen (SPA) or Her-2/neu, KSA (GA733) MUC-1 and carcinoembryonic antigen (CEA). Other antigens have been put forward as being pan-cancer therapeutic antigens including luteinizing hormone-releasing hormone (gonadotropin-releasing hormone) ("LnRH(GnRH)", Tyrosinase and Survivin. Accordingly in one aspect of the present invention there is provided a vaccine comprising an adjuvant composition according to the invention and a tumour rejection antigen.

It is foreseen that compositions of the present invention will be used to formulate vaccines containing antigens derived from *Borrelia* sp. For example, antigens may include nucleic acid, pathogen derived antigen or antigenic preparations, recombinantly produced protein or peptides, and chimeric fusion proteins. In particular the antigen is OspA. The OspA may be a full mature protein in a lipidated form virtue of the host cell (*E. Coli*) termed (Lipo-OspA) or a non-lipidated derivative. Such non-lipidated derivatives include the non-lipidated NS1-OspA fusion protein which has the first 81 N-terminal amino acids of the non-structural protein (NS1) of the influenza virus, and the complete OspA protein, and another, MDP-OspA is a non-lipidated form of OspA carrying 3 additional N-terminal amino acids.

Vaccines of the present invention may be used for the prophylaxis or therapy of allergy. Such vaccines would comprise allergen specific (for example Der p1, and pollen related antigens) and allergen non-specific antigens (for example the stanworth decapeptide).

The amount of antigen in each vaccine dose is selected as an amount which induces an immunoprotective response without significant, adverse side effects in typical vaccinees. Such amount will vary depending upon which specific immunogen is employed and how it is presented. Generally, it is expected that each dose will comprise 1–1000 μg of antigen, preferably 1–500 μg, preferably 1–100 μg, most preferably 1 to 50 μg. An optimal amount for a particular vaccine can be ascertained by standard studies involving observation of appropriate immune responses in subjects. Following an initial vaccination, subjects may receive one or several booster immunisation adequately spaced. Typically for human administration the immunostimulant will be present in the range 1 μg –1000 μg, preferably 10 μg –500 μg, more preferably 20–200 μg per dose, more preferably 20–1001 μg per dose, and most preferably 10–50 μg per dose.

The present invention further provides for the adjuvants and vaccines of the present invention for use in medicine, specifically as a method of treating a mammal suffering from or susceptible to a pathogenic infection, or cancer, or allergy. Also provided for is the use of the adjuvants and vaccines of the present invention in the manufacture of a immunoprophylactic and immunotherapeutic treatment of viral, bacterial, parasitic infections, allergy, or cancer. The formulations of the present invention maybe used for both prophylactic and therapeutic purposes.

Vaccine preparation is Generally described in "Vaccine Design—the subunit and adjuvant approach" Edited by Powell, M. F. and Newman, M. J.; 1995, Pharmaceutical Biotechnology (Plenum Press, New York and London, ISBN 0-306-44867-X).

The present invention is illustrated by, but not restricted to, the following examples.

EXAMPLE 1

Materials and Methods

Serology

Quantification of anti-HBs antibody was performed by ELISA using HBs (Hep 286) as coating antigen. Antigen and antibody solutions were used at 50 Al per well. Antigen was diluted at a final concentration of 1 μg/ml in PBS and was adsorbed overnight at 4° C. to the wells of 96 wells microtiter plates (Maxisorb Immuno-plate, Nunc. Denmark). The plates were then incubated for 1 hr at 37° C. with PBS containing 1% bovine serum albumin and 0.1% TWEEN 20 (saturation buffer; 100 μl/well). Two-fold dilutions of sera (starting at 1/100 dilution) in the saturation buffer were added to the HBs-coated plates and incubated for 1 hr 30 min at 37° C. The plates were washed four times with PBS 0.1% TWEEN 20 and biotin-conjugated anti-mouse IgG1, IgG2a, IgG2b or Ig (Amersham, UK) diluted 1/1000 in saturation buffer was added to each well and incubated for 1 hr 30 min at 37° C. After a washing step, streptavidin-biotinylated peroxidase complex (Amersham, UK) diluted 1/5000 in saturation buffer was added for an additional 30 min at 37° C. Plates were washed as above and incubated for 20 min with a solution of o-phenylenediamine (Sigma) 0.04% $H_2O_2$ 0.03% in 0.1% TWEEN 20, 0.05M citrate buffer pH 4.5. The reaction was stopped with $H_2SO_4$ 2N and read at 490/630 nm. ELISA titers were calculated from a reference by SoftmaxPro (using a four parameters equation) and expressed in EU/ml.

T Cell Proliferation 2 weeks after the second immunisation, mice were killed, spleens were removed aseptically in pools. Cell suspensions were prepared in RPMI 1640 medium (GIBCO) containing 2 mM L-glutamine, antibiotics, $5\times10^{-5}$ M 2-mercaptoethanol, and 1% syngeneic normal mouse serum. Splenic cells were cultured at a final concentration of $2\times10^6$ cells/ml in 200 μl in round-bottomed 96 wells-plates with different concentrations (10–0.03 μg/ml) of HBs antigen. Each test was carried out in quadruplicate. After 96 hr of culture at 37° C. under 5% $CO_2$, the cells were pulsed for 18 hr with $^3$H-Thymidine (Amersham, UK, 5 Ci/mmol) at 0.5 μCi/well and then harvested on Unifilter plates (Packard) with a cell harvester. Incorporated radioactivity was measured in a scintillation counter (Topcount, Packard). Results are expressed in cpm (mean cpm in quadruplicate wells) or as stimulation indices (mean cpm in cultures of cells with antigen/mean cpm in cultures of cells without antigen).

Cytokine Production 2 weeks after the second immunisation, mice were killed, spleens were removed aseptically in pools (3 pools per group). Cell suspensions were prepared in RPMI 1640 medium (GIBCO) containing 2 mM L-glutamine, antibiotics, $5\times10^{-5}$ M 2-mercaptoethanol, and 5% foetal calf serum.

Cells were cultured at a final concentration of $5\times10^6$ cells/ml in 1 ml, in flat-bottomed 24 wells-plates with different concentrations (10-0.1 µg/ml) of HBs antigen. Supernatants were harvested 96 hrs later and frozen until tested for the presence of IFNγ and IL-5 by ELISA.

IFNγ Production

Quantification of IFNγ was performed by ELISA using reagents from Genzyme. Samples and antibody solutions were used at 50 µl per well. 96-wells microtiter plates (Maxisorb Immuno-plate, Nunc, Denmark) were coated overnight at 4° C. with 50 µl of hamster anti-mouse IFNγ diluted at 1.5 µg/ml in carbonate buffer pH 9.5. Plates were then incubated for 1 hr at 37° C. with 100 µl of PBS containing 1% bovine serum albumin and 0.1% TWEEN 20 (saturation buffer). Two-fold dilutions of supernatant from in vitro stimulation (starting at ½) in saturation buffer were added to the anti-IFNγ-coated plates and incubated for 1 hr 30 at 37° C. The plates were washed 4 times with PBS TWEEN 0.1% (wash buffer) and biotin-conjugated goat anti-mouse IFNγ diluted in saturation buffer at a final concentration of 0.5 µg/ml was added to each well and incubated for 1 hr at 37° c. After a washing step, AMDEX conjugate (Amersham) diluted 1/10000 in saturation buffer was added for 30 min at 37° C. Plates were washed as above and incubated with 50 µl of TMB (Biorad) for 10 min. The reaction was stopped with $H_2SO_4$ 0.4N and read at 450/630 nm. Concentrations were calculated using a standard curve (mouse IFNγ standard) by SoftmaxPro (four parameters equation) and expressed in pg/ml.

IL-5 Production

Quantification of IL-5 was performed by ELISA using reagents from Pharmingen. Samples and antibody solutions were used at 50 µl per well. 96-wells microtiter plates (Maxisorb Immuno-plate, Nunc, Denmark) were coated overnight at 4° C. with 50µ of rat anti-mouse IL-5 diluted at 1 µg/ml in carbonate buffer pH 9.5. Plates were then incubated for 1 hr at 37° C. with 100 µl PBS containing 1% bovine serum albumin and 0.1% TWEEN 20 (saturation buffer). Two-fold dilutions of supernatant from in vitro stimulation (starting at 1/2) in saturation buffer were added to the anti-IFNγ-coated plates and incubated for 1 hr 30 at 37° C. The plates were washed 4 times with PBS TWEEN 0.1% (wash buffer) and biotin-conjugated rat anti-mouse IL-5 diluted in saturation buffer at a final concentration of 1 µg/ml was added to each well and incubated for 1 hr at 37° C. After a washing step, AMDEX conjugate (Amersham) diluted 1/10000 in saturation buffer was added for 30 min at 37° C. Plates were washed as above and incubated with 50 µl of TMB (Biorad) for 15 min. The reaction was stopped with $H_2SO_4$ 0.4N and read at 450/630 nm. Concentrations were calculated using a standard curve (recombinant mouse IL-5) by SoftmaxPro (four parameters equation) and expressed in pg/ml.

EXAMPLE 2

Immunogenicity Studies in Mice

In order to test the concept of MPL on a solid particulate carrier free of antigen, an immunogenicity study was performed in Balb/C mice using various sequences of formulations of HABMPL vaccines:

TABLE 1

| | Vaccine formulations |
|---|---|
| Group | Formulation |
| 1 | $(HB-AlPO_4)$ − 3D-MPL + $(HA-Al(OH)_3)$ |
| 2 | $(3D-MPL-Al(OH)_3)$ + $(HA-Al(OH)_3)$ + $(HB-AlPO_4)$ |
| 3 | $(3D-MPL-AlPO_4)$ + $(HA-Al(OH)_3)$ + $(HB-AlPO_4)$ |

Description of Formulation Process:

Group 1, The formulation process of the prior art. The antigen is first adsorbed onto the metallic salt followed by the addition of free 3D-MPL, resulting in the adsorption of the 3D-MPL onto the same particle of metallic salt as the antigen.

Group 2 and 3, The formulation process of the present invention. The 3D-MPL is adsorbed onto one particle of metallic salt, the antigens are adsorbed onto separate particles of metallic salt, followed by the admixture of the pre-adsorbed complexes.

Immunisation Scheme

Groups of 10 mice were immunised subcutaneously twice at 4 weeks interval with HAB based formulations (1/10Human Dose, i.e. HAV 72 ELU, HBs 2 µg, MPL 5 µg). On day 14 post II, lymphoproliferative response and cytokine production (IL5/IFNγ) were analysed after in vitro restimulation of splenic cells with HBs and HAV. Blood was taken from the retroorbital sinus on day 35 and antibody response to HBs and HAV as well as the isotypic profile induced (HBs only) were monitored by ELISA.

Results

Humoral responses (Ig and isotopes) were measured by ELISA using HBs as coating antigen for HBV and using the Behring kit for HAV. Only 14 days post II bleeding was analysed.

FIG. 1 shows anti-HBs Ig antibody responses measured on individual sera and represented as GMT.

FIG. 2 shows the isotypic repartition (IgG1, IgG2a and IgG2b) calculated from analysis on pooled sera.

No differences in antibody titers are observed between group 1 and the novel formulations (groups 2 and 3). Furthermore, the novel formulations (groups 2 and 3) stimulate similar proportions of IgG1 and IgG2a/b isotypes as those stimulated by the formulations of the prior art (group 1).

Cell-Mediated Immune Responses

Cell-mediated immune responses (lymphoproliferation and IFNγIL-5 production) were measured at 14 days post II after in vitro restimulation of splenic cells with HBs or HA antigens. For each group of mice, 5 animals were sacrificed and spleens pooled for in vitro testing.

FIG. 3 shows the lymphoproliferation monitored in splenic cells restimulated with HBs.

FIG. 4 shows the cytokine production monitored in splenic cells restimulated with HBs.

No differences lymphoproliferative responses can be observed between the formulations.

Strong IFN-γ (+/−1000 pg/ml) responses were observed with all groups, moreover, no difference in IL-5 production (below 60 pg/ml) is observed between the groups.

Conclusions

No significant differences in humoral and cell-mediated immune responses to HBsAg were observed between the HABMPL formulation sequences.

EXAMPLE 3

HSV Vaccination of Guinea Pigs

The previous example demonstrated the efficacy of the new formulations and processes, with respect to Hepatitis antigens. This example investigated the immunogenicity and protective efficacy of Herpes Simplex Virus gD vaccines formulated with alum and 3D-MPL in the classical process in comparison with the process of the present invention. The two vaccines were compared in the HSV Guinea pig intra-vaginal protection model.

| Group | Formulations |
|---|---|
| 4 | gD2t (20 μg) + 3D-MPL (50 μg) + AlOH (500 μg) |
| 5 | gD2t (20 μg) + AlOH (400 μg) <br> 3D-MPL (50 μg) + AlOH (100 μg) |
| 6 | Untreated |

Experimental protocol

Groups of 12 female Hartley guinea pigs were immunised twice at days 0 and 28. At day 57, the animals were challenged intra-vaginally with 105 pfu of HSV2 MS strain (100 μl). After challenge, animals were monitored daily for clinical signs of primary disease from day 4 to 12. Blood was taken from the retro-orbital sinus at days 14 and 28 after the second immunisation and the anti-gD antibody response (IgG) was monitored by ELISA.

Formulation Process gD2t from HSV2 was produced according to techniques described in WO 92/16231. 3D-MPL was purchased from Ribi ImmunoChem Inc., Montana, USA. AlOH3 was purchased from Superfos. Formulations were prepared 15 days before the first injection. All incubations were carried out at room temperature with agitation.

Group 4 Al(OH)$_3$-Based Formulations (250 μl/Dose): Classical Way gD2t (5 μg) was adsorbed on 125 μg of Al(OH)$_3$ for 15 min before MPL addition (12.5 μg). Thirty minutes later, the formulation was buffered with a 10-fold concentrated PBS pH 7.4 solution. After 15 min, 500 μg/ml of phenoxyethanol was added as preservative.

H2O+Al(OH)3+Ag-15m-MPL-30m-10xPBSpH7.4-15m-2 phenoxy

Group 5 Al(OH)3-Based Formulations (250 μl/Dose): New Way gD2t (5 μg) was adsorbed on 100 μg of Al(OH)$_3$ for 15 min and stocked as a concentrated monobulk. In an other hand. MPL (12.5 μg) was adsorbed on 25 μg of Al(OH)$_3$ for 30 min and stocked as an other concentrated monobulk. For the final formulation, the adsorbed gD2t was diluted in H2O and 10-fold concentrated PBS pH 7.4. Fifteen minutes later, adsorbed MPL was added before phenoxyethanol addition as preservative.

Al(OH)3+Ag
Al(OH)3+MPL
H2O+10×PBS pH 7.4+Ads gD2t-15m-Ads MPL-15m$^{-2}$ phenoxy Sample Quantification Quantification of anti-gD antibody was performed by Elisa using gD 43B318 as coating antigen. Antigen and antibody solutions were used at 50 μl per well. Antigen was diluted at a final concentration of 1 μg/ml in PBS and was adsorbed overnight at 4° C. to the wells of 96 wells microtiter plates (Maxisorb Immuno-plate, Nunc, Denmark). The plates were then incubated for 1 hr at 37° C. with PBS containing 1% bovine serum albumin and 0.1% Tween 20 (saturation buffer). Two-fold dilutions of sera in the saturation buffer were added to the gD-coated plates and incubated for 1 hr 30 min at 37° C. The plates were washed four times with PBS 0.1% Tween 20 and biotin-conjugated anti-guinea pig IgG (Amersham, UK) diluted 1/10000 in saturation buffer was added to each well and incubated for 1 hr 30 min at 37° C. After a washing step, streptavidin-biotinylated peroxydase complex (Amersham, UK) diluted 1/1000 in saturation buffer was added for an additional 30 min at 37° C. Plates were washed as above and incubated for 20 min with a solution of o-phenylenediamine (Sigma) 0.04% H2O2 0.03% in 0.1% tween 20 0.05M citrate buffer pH4.5. The reaction was stopped with H2SO4 2N and read at 490/630 nm. ELISA titers were calculated from a reference by SoftmaxPro (using a four parameters equation) and expressed in EU/ml.

Stastical Analysis

Statistical analyses were performed on serology data using UNISTAT:

The protocol applied for one way analysis of variance can be briefly described as follows:
1) Log transformation of data.
2) Kolmogorov Smirnov test on each population (group) in order to verify the normality.
3) Hartley and Cochran tests in order to verify the homogeneity of variance between the different populations (groups).
4) Analysis of variance on selected data: 14 days post II or 28 days post II data.

Results

Serology

FIG. 5, shows anti-gD IgG antibody responses measured at post II on individual sera.

No striking difference in antibody titers is observed between either formulations at day 14 post II (17090–18508 EU/ml for GMT) or 28 days post II (10227–11965 EU/ml for GMT). One way analysis of variance was performed separately on anti-gD IgG titres raised by either vaccine formulation, from both time-points after Log transformation of data. No statistically significant differences between either formulations were detected (p–values 0.7397 and 0.5078 for respectively 14 days post II and 28 days post II data).

Protection from Disease

Protection against primary disease was evaluated between 4 to 12 days post challenge, by comparing several parameters in vaccinated and untreated animals:

The percentage of animals with and without lesions (vaginal or external).

The primary infection index (PI) calculated for each group as follows:

Σ (score maximum×incidence expressed in %).

The sum of lesion scores (day 4 to 12) expressed as median and the number of animals showing lesions (N).

The mean cumulative scores calculated for each group between day 4 and 12

TABLE 2 summarises the lesion parameters

| Group | Animals without lesions (%) | Vaginal lesions (%) | External lesions (%) | Primary infection index* | Lesion severity (n)** |
|---|---|---|---|---|---|
| 4 | 66.7 | 25 | 8.3 | 29.2 −97% | 1 (4) |
| 5 | 83.3 | 16.7 | 0 | 8.3 −99% | 0.5 (2) |
| 6 | 11.1 | 0 | 88.9 | 844.4 | 28.3 (8) |

*Sum of lesion scores for the days 4 to 12 post-infection (animals without lesions were not considered). Lesion scores: no lesion (0), vaginal lesions (0.5 or 1), external skin vesicles (2, 4, 8 or 16).
**Primary infection index = (max score I) × (incidence %); with I = 0, 0.5, 1, 2, 4, 8 or 16.

FIG. 6 shows the cumulative lesion score curves after HSV challenge.

A high percentage of vaccinated animals did not develop any lesion (66% to 83%) or developed vaginal lesions. In comparison, 89% of the animals of the control group showed external lesions.

A strong reduction of primary infection index was observed in vaccinated animals (97% to 99%). This was accompanied with a very low lesion severity was recorded for the vaccinated groups (median=0.5 or 1) compared to the untreated group (median=28).

As shown by the curves of cumulative scores both groups (4 and 5) gave a very good and comparable level of protection against primary disease Conclusion Old and new processes for vaccine HSV vaccine formulation were compared. No statistically significant difference was observed between the two processes in either IgG titres or in protection against primary disease.

EXAMPLE 4

HPV Vaccination of Mice

Various sequences of formulations (AlOH or AlPO4 based) of Human Papiloma Virus E7 antigen and 3D-MPL were compared regarding their capacity to induce antigen-specific humoral responses. Comparable Ig titers are obtained with formulations with mixed adsorption of 3D-MPL and proteinD 1/3-E7 on the same carrier (way 1) and formulations where 3D-MPL is adsorbed separately on a carrier free of antigen (way 2). Protein D 1/3 E7 were prepared according to the procedure of WO 99/10375. The antigen and MPL formulations were either AlOH-based or AlPO4-based.

Antigen and 3D-MPL were adsorbed sequentially to the same particles of Aluminium salt (way 1), or separate absorptions were made prior to mixing (way 2).

Groups of 10 mice were immunized using the following formulations (description in Material and Methods):

| Group | Description | Formulation |
|---|---|---|
| 7 | ProtD 1/3 E7-AlOH | 5 μg ProtD 1/3 E7 adsorbed on AlOH |
| 8 | ProtD 1/3 E7-AlOH/MPL | 5 μg ProtD 1/3 E7 adsorbed on AlOH with MPL (way 1) |
| 9 | ProtD 1/3 E7-AlOH/ (ALPO4/MPL) | 5 μg ProtD 1/3 E7 adsorbed on AlOH combined with MPL adsorbed on AlPO4 (way 2) |
| 10 | ProtD 1/3 E7-AlPO4 | 5 μg ProtD 1/3 E7 adsorbed on AlPO4 |
| 11 | ProtD 1/3 E7-AlPO4/MPL | 5 μg ProtD 1/3 E7 adsorbed on AlPO4 with MPL (way 1) |
| 12 | ProtD 1/3 E7-AlPO4/ (AlOH/MPL) | 5 μg ProtD 1/3 E7 adsorbed on AlPO4 combined with MPL adsorbed on AlOH (way 2) |
| 13 | ProtD 1/3 E7 o/w | 5 μg ProtD 1/3 E7 formulated in oil in water emulsion 3D-MPL/ QS21 |

Mice were immunized twice at a 21-day interval by the intramuscular route. Sera were collected on Day 35 (14 days post II) and analysed for the presence of E7 specific antibodies (see Material and Methods). Formulations were prepared 5 days before the first injection. All incubations were carried out at room temperature with agitation.

I. Al-Based Formulations (50 μl/Dose): Classical Way (Way 1)

PD1/3E7 (5 μg) was adsorbed on 50 μg of $Al(OH)_3$ or AlPO4 for 30 min before MPL addition (5 μg). Thirty minutes later, the formulation was buffered with a 10-fold concentrated PO4, NaCl pH 6.8 solution. After 15 min. 50 μg/ml of thiomersal was added as preservative.

H2O+Al+Ag-30m-MPL-30m-10xPNpH6.8-15m-Thio

II. Al-Based Formulations (50/1/Dose): New Way (Way 2)

PD1/3E7 (5 μg) was adsorbed on 0 μg of $Al(OH)_3$ or AlPO4 for 30 min and stocked as concentrated monobulks. In an other hand, MPL (5 μg) was adsorbed on 20 μg of $Al(OH)_3$ or AlPO4 for 30 min and stocked as others concentrated monobulks. For the final formulations, the adsorbed antigen was diluted in H2O and 10-fold concentrated PO4, NaCl pH 6.8 solution before addition of the adsorbed MPL and of the rest of Al (20 μg). Thirteen minutes later, 50 μg/ml of thiomersal was added as preservative.

Al+Ag

Al+MPL

H20+10xPN pH 6.8+Ads PD1/3E7+Ads MPL+Al-30m-Thio

Serology

Quantification of anti-E7 antibody was performed by Elisa using E7 (Bollen) as coating antigen. Antigen and antibody solutions were used at 50 μl per well. Antigen was diluted at a final concentration of 3 μg/ml in carbonate buffer ph9.5 and was adsorbed overnight at 4° C. to the wells of 96 wells microtiter plates (Maxisorb Immuno-plate, Nunc, Denmark). The plates were then incubated for 1 hr at 37° C. with PBS containing 1% bovine serum albumin and 0.1% Tween 20 (saturation buffer). Two-fold dilutions of sera (starting at 1/100 dilution) in the saturation buffer were added to the E7-coated plates and incubated for 1 hr 30 min at 37° C. The plates were washed 3 times with PBS 0.1% Tween 20 and biotin-conjugated anti-mouse (IgG1. IgG2a or IgG2b or) IgGtot (Amersham, UK) diluted 1/5000 in saturation buffer was added to each well and incubated for 1 hr 30 min at 37° C. After a washing step, streptavidin-biotinylated peroxydase complex (Amersham, UK) diluted 1/5000 in saturation buffer was added for an additional 30 min at 37° C. Plates were washed as above and incubated for 10 min with TMB (tetra-methyl-benzidine). The reaction was stopped with H2SO4 4N and read at 450 nm. Midpoint dilutions were calculated by SoftmaxPro (using a four parameters equation).

Results

The anti-E7 Ig titers measured on pooled sera by ELISA expressed in EU/ml are as follows

|  | E7-AlOH based formulations | E7-AlPO4 based formulations |
| --- | --- | --- |
| Alum | 4434 | 1651 |
| Alum/MPL | 10780 | 12666 |
| Alum/(Alum/MPL) | 13390 | 15495 |

Comparable titers are obtained when comparing the AlOH based formulations or the AlPO4 based formulations. When MPL is added to the AlOH or AlPO4 formulations, the titers reached are above 10,000 EU/ml as compared to less than 5,000 EU/ml for the Al formulations. Comparable titers are obtained with both formulation sequences.

Various sequences of formulations (AlOH or AlPO4 based) of antigen and MPL were compared regarding their capacity to induce the production of antigen-specific antibodies:

All formulations containing MPL induce higher levels of E7-specific Ig than Alum formulations. Comparable Ig titers are obtained with formulations with mixed adsorption of MPL and pD1/3-E7 on the same carrier (way 1) and formulations where MPL is adsorbed separately on a carrier free of antigen (way 2).

What is claimed is:

1. A process for the manufacture of a vaccine composition comprising admixing a) an adjuvant composition containing an immunostimulant adsorbed onto a first metallic salt particle substantially free of antigen, and b) an antigen, wherein the antigen is adsorbed onto a second metallic salt particle substantially free of immunostimulant, wherein the metallic salt of each of the first metallic salt particle and the second metallic salt particle may be the same.

2. A process for the manufacture of an immunogenic composition comprising admixing a) an adjuvant composition containing an immunostimulant adsorbed onto a first metallic salt particle substantially free of antigen, and b) an antigen, wherein the antigen is adsorbed onto a second metallic salt particle substantially free of immunostimulant wherein the metallic salt of each of the first metallic salt particle and the second metallic salt particle may be the same and wherein the antigen of b) elicits an immune response to a pathogen, polypeptide, or anti-tumour antigen selected from the group consisting of antigens derived from Human Immunodeficiency Virus, Varicella Zoster virus, Herpes Simplex Virus type 1, Herpes Simplex Virus type 2, Human cytomegalovirus, Dengue virus, Hepatitis A, B, C or E, Respiratory Syncytial virus, human papilloma virus, Influenza virus, *Haemophilus influenzae* Type B ("Hib"), Meningitis virus, *Salmonella, Neisseria, Borrelia, Chlamydia, Bordetella, Plasmodium* or *Toxoplasma*, IgE peptides, Der p1, pollen related antigens; or Tumor associated antigens (TAA), MAGE, BAGE, GAGE, MUC-1, Her-2 neu, luteinizing hormone-releasing hormone (gonadotropin-releasing hormone), CEA, PSA, KSA, and PRAME.

3. The process of claim 2, wherein the antigen elicits an immune response to human papilloma virus (HPV).

4. The process of claim 3, wherein the HPV is selected from the group consisting of: HPV 6, HPV 11, HPV 16 and HPV 18.

5. The process of claim 3, wherein the antigen is an L1 particle or capsomer.

6. A vaccine composition comprising an adjuvant composition and an antigen, wherein the adjuvant composition contains an immunostimulant adsorbed onto a metallic salt particle, wherein the metallic salt particle is substantially free of the antigen and wherein the immunostimulant is selected from the group consisting of monophosphoryl lipid A, derivatives thereof, an immunostimulatory nucleotide, and an immunostimulatory cytokine.

7. The vaccine composition of claim 6, wherein the immunostimulant is 3-de-O-acylated monophosphoryl lipid A.

8. The vaccine composition of claim 6, wherein the antigen is a combination of Hepatitis A antigen and Hepatitis B antigen.

9. The vaccine composition of claim 6, wherein the antigen is RTS,S.

10. A method of treating a mammal suffering from or susceptible to a pathogenic infection, or allergy, comprising the administration of the vaccine composition of claim 6.

11. The vaccine of to claim 6 wherein the antigen elicits an immune response to human papilloma virus (HPV).

12. The vaccine composition according to claim 11, wherein the HPV is selected from the group of: HPV 6, HPV 11, HPV 16 and HPV 18.

13. The vaccine composition of claim 11, wherein the antigen is an L1 particle or capsomer.

14. A vaccine composition comprising two major populations of complexes, (a) a first complex containing an immunostimulant adsorbed onto a metallic salt particle which is substantially free of antigen; and (b) a second complex containing antigen adsorbed onto a metallic salt particle which is optionally substantially free of immunostimulant; wherein the metallic salt from the first complex may be identical to or different from the metallic salt of the second complex.

15. The vaccine composition of claim 14, wherein the immunostimulant is 3-de-O-acylated monophosphoryl lipid A.

16. The vaccine composition of claim 14, wherein the antigen is a combination of Hepatitis A antigen and Hepatitis B antigen.

17. The vaccine composition of claim 14, wherein the antigen is RTS,S.

18. A method of treating a mammal suffering from or susceptible to a pathogenic infection, or allergy, comprising the administration of the vaccine composition of claim 6.

19. The vaccine composition of claim 14, wherein the metallic salt present in the first and second complexes are identical.

20. The vaccine composition of claim 19, wherein the immunostimulant is 3-de-O-acylated monophosphoryl lipid A.

21. The vaccine composition of claim 19, wherein the antigen is a combination of Hepatitis A antigen and Hepatitis B antigen.

22. The vaccine composition of claim 19, wherein the antigen is RTS,S.

23. A method of treating a mammal suffering from or susceptible to a pathogenic infection, or allergy, comprising the administration of the vaccine composition of claim 19.

24. The vaccine composition of claim 14, wherein the second complex contains a plurality of subpopulations of complexes, each subpopulation containing an antigen adsorbed onto a metallic salt particle wherein each subpopulation contains a different antigen.

25. The vaccine composition of claim 24, wherein the immunostimulant is 3-de-O-acylated monophosphoryl lipid A.

26. The vaccine composition of claim 24, wherein the antigen is a combination of Hepatitis A antigen and Hepatitis B antigen.

27. The vaccine composition of claim 24, wherein the antigen is RTS,S.

28. A method of treating a mammal suffering from or susceptible to a pathogenic infection, or allergy, comprising the administration of the vaccine composition of claim 24.

29. The vaccine composition of claim 14, wherein the metallic salt is a salt of aluminum, zinc, calcium, cerium, chromium, iron, or berylium.

30. The vaccine composition of claim 29, wherein the immunostimulant is 3-de-O-acylated monophosphoryl lipid A.

31. The vaccine composition of claim 19, wherein the antigen is a combination of Hepatitis A antigen and Hepatitis B antigen.

32. The vaccine composition of claim 29, wherein the antigen is RTS,S.

33. A method of treating a mammal suffering from or susceptible to a pathogenic infection, or allergy, comprising the administration of the vaccine composition of claim 29.

34. The vaccine composition of claim 29 wherein the metallic salt is a phosphate or hydroxide.

35. The vaccine composition of claim 34, wherein the immunostimulant is 3-de-O-acylated monophosphoryl lipid A.

36. The vaccine composition of claim 34, wherein the antigen is a combination of Hepatitis A antigen and Hepatitis B antigen.

37. The vaccine composition of claim 34, wherein the antigen is RTS,S.

38. A method of treating a mammal suffering from or susceptible to a pathogenic infection, or allergy, comprising the administration of the vaccine composition of claim 34.

39. The vaccine composition of claim 34 wherein the metallic salt is aluminium hydroxide or aluminium phosphate.

40. The vaccine composition of claim 39, wherein the immunostimulant is 3-de-O-acylated monophosphoryl lipid A.

41. The vaccine composition of claim 39, wherein the antigen is a combination of Hepatitis A antigen and Hepatitis B antigen.

42. The vaccine composition of claim 39, wherein the antigen is RTS,S.

43. A method of treating a mammal suffering from or susceptible to a pathogenic infection, or allergy, comprising the administration of the vaccine composition of claim 39.

44. A vaccine composition comprising: a) an immunostimulant adsorbed onto a metallic salt particle, wherein the immunostimulant is selected from the group consisting of bacterially derived compounds, monophosphoryl lipid A, immunostimulatory oligonucleotides, CpG, block copolymers, cholera toxin, immunostimulatory cytokines, GM-CSF, IL-1, polyriboA, polyriboU, and Muramyl tripeptide, and b) an antigen, wherein the antigen is not adsorbed onto the metallic salt particle.

45. An immunogenic composition comprising an adjuvant composition and an antigen, wherein the adjuvant composition contains an immunostimulant adsorbed onto a metallic salt particle, wherein the metallic salt particle is substantially free of the antigen and wherein the immunostimulant is selected from the group consisting of monophosphoryl lipid A, derivatives thereof, an immunostimulatory nucleotide, and an immunostimulatory cytokine.

46. The immunogenic composition of claim 45, wherein the antigen elicits an immune response against a pathogen, polypeptide, or anti-tumour antigen selected from the group consisting of: Human Immunodeficiency Virus, Varicella Zoster virus, Herpes Simplex Virus type 1, Herpes Simplex virus type 2, Human cytomegalovirus, Dengue virus, Hepatitis A, B, C or E, Respiratory Syncytial virus, Human papilloma virus, Influenza virus, *Haemophilus influenzae* Type B ("Hib"), Meningitis virus, *Salmonella, Neisseria, Borrelia, Chlamydia, Bordetella, Plasmodium* or *Toxoplasma*, stanworth decapeptide, Der p1, pollen related antigens; or cancer associated antigens, MAGE, BAGE, GAGE, MUC-1, Her-2 neu, luteinizing hormone-releasing hormone (gonadotropin-releasing hormone), CEA, PSA, tyrosinase, Survivin, KSA, PRAME, RTS, S, *P. faciparum* MSP1, *P. faciparum* AMA1, *P. faciparum* MSP3, *P. faciparum* EBA, *P. faciparum* GLURP, *P. faciparum* RAP1, *P. faciparum* RAP2, *P. faciparum* Sequestrin, *P. faciparum* PfEMP1, *P. faciparum* Pf332, *P. faciparum* LSA1, *P. faciparum* LSA3, *P. faciparum* STARP, *P. faciparum* SALSA, *P. faciparum* PfEXPa, *P. faciparum* Pfs25, *P. faciparum* Pfs28, *P. faciparum* PFS27/25, *P. faciparum* Pfs16, *P. faciparum* Pfs48/45, *P. faciparum* Pfs230, and any analogues of *P. faciparum* antigens from *Plasmodium* ssp.

47. An immunogenic composition comprising two populations of complexes, a first complex comprising, (a) a first complex containing an immunostimulant adsorbed onto a metallic salt particle, which is substantially free of antigen; and (b) a second complex containing antigen adsorbed onto a metallic salt particle which is optionally substantially free of immunostimulant; wherein the metallic salt from the first complex may be identical to or different from the metallic salt of the second complex.

48. The immunogenic composition of claim 47, wherein the antigen elicits an immune response against a pathogen, polypeptide, or anti-tumour antigen selected from the group consisting of: Human Immunodeficiency Virus, Varicella Zoster virus, Herpes Simplex Virus type 1, Herpes Simplex virus type 2, Human cytomegalovirus, Dengue virus, Hepatitis A, B, C or E, Respiratory Syncytial virus, Human papilloma virus, Influenza virus, *Haemophilus influenzae* Type B ("Hib"), Meningitis virus, *Salmonella, Neisseria, Borrelia, Chlamydia, Bordetella, Plasmodium* or *Toxoplasma*, stanworth decapeptide, Der p1, pollen related antigens; or cancer associated antigens, MAGE, BAGE, GAGE, MUC-1, Her-2 neu, luteinizing hormone-releasing hormone (gonadotropin-releasing hormone), CEA, PSA, tyrosinase, Survivin, KSA, PRAME, RTS, S, *P. faciparum* MSP1, *P. faciparum* AMA1, *P. faciparum* MSP3, *P. faciparum* EBA, *P. faciparum* GLURP, *P. faciparum* RAP1, *P. faciparum* RAP2, *P. faciparum* Sequestrin, *P. faciparum* PfEMP1, *P. faciparum* Pf332, *P. faciparum* LSA1, *P. faciparum* LSA3, *P. faciparum* STARP, *P. faciparum* SALSA, *P. faciparum* PfEXPa, *P. faciparum* Pfs25, *P. faciparum* Pfs28, *P. faciparum* PFS27/25, *P. faciparum* Pfs16, *P. faciparum* Pfs48/45, *P. faciparum* Pfs230, and any analogues of *P. faciparum* antigens from *Plasmodium* ssp.

49. The immunogenic composition of claim 47, wherein the metallic salt present in the first complex is identical to the metallic salt present in the second complex.

50. The immunogenic composition of claim 49, wherein the antigen elicits an immune response against a pathogen, polypeptide, or anti-tumour antigen selected from the group consisting of: Human Immunodeficiency Virus, Varicella Zoster virus, Herpes Simplex Virus type 1, Herpes Simplex virus type 2, Human cytomegalovirus, Dengue virus, Hepatitis A, B, C or E, Respiratory Syncytial virus, Human papilloma virus, Influenza virus, *Haemophilus influenzae* Type B ("Hib"), Meningitis virus, *Salmonella, Neisseria, Borrelia, Chlamydia, Bordetella, Plasmodium* or *Toxoplasma*, stanworth decapeptide, Der p1, pollen related antigens; or cancer associated antigens, MAGE, BAGE, GAGE, MUC-1, Her-2 neu, luteinizing hormone-releasing hormone (gonadotropin-releasing hormone), CEA, PSA, tyrosinase, Survivin, KSA, PRAME, RTS, S, *P. faciparum* MSP1, *P. faciparum* AMA1, *P. faciparum* MSP3, *P. faciparum* EBA, *P. faciparum* GLURP, *P. faciparum* RAP1, *P. faciparum* RAP2, *P. faciparum* Sequestrin, *P. faciparum* PfEMP1, *P. faciparum* Pf332, *P. faciparum* LSA1, *P. faciparum* LSA3, *P. faciparum* STARP, *P. faciparum* SALSA, *P. faciparum* PfEXPa, *P. faciparum* Pfs25, *P. faciparum* Pfs28, *P. faciparum* PFS27/25, *P. faciparum* Pfs16, *P. faciparum* Pfs48/45, *P. faciparum* Pfs230, and any analogues of *P. faciparum* antigens from *Plasmodium* ssp.

51. The immunogenic composition of claim 47, wherein the second complex contains a plurality of subpopulations of complexes, each subpopulation containing an antigen adsorbed onto a metallic salt particle wherein each subpopulation contains a different antigen.

52. The immunogenic composition of claim 51, wherein the antigen elicits an immune response against a pathogen, polypeptide, or anti-tumour antigen selected from the group consisting of: Human Immunodeficiency Virus, Varicella Zoster virus, Herpes Simplex Virus type 1, Herpes Simplex virus type 2, Human cytomegalovirus, Dengue virus, Hepatitis A, B, C or E, Respiratory Syncytial virus, Human papilloma virus, Influenza virus, *Haemophilus influenzae* Type B ("Hib"), Meningitis virus, *Salmonella, Neisseria, Borrelia, Chlamydia, Bordetella, Plasmodium* or *Toxoplasma*, stanworth decapeptide, Der p1, pollen related antigens; or cancer associated antigens, MAGE, BAGE, GAGE, MUC-1, Her-2 neu, luteinizing hormone-releasing hormone (gonadotropin-releasing hormone), CEA, PSA, tyrosinase, Survivin, KSA, PRAME, RTS, S, *P. faciparum* MSP1, *P. faciparum* AMA 1, *P. faciparum* MSP3, *P. faciparum* EBA, *P. faciparum* GLURP, *P. faciparum* RAP 1, *P. faciparum* RAP2, *P. faciparum* Sequestrin, *P. faciparum* PfEMP1, *P. faciparum* Pf332, *P. faciparum* LSA1, *P. faciparum* LSA3, *P. faciparum* STARP, *P. faciparum* SALSA, *P. faciparum* PfEXPa, *P. faciparum* Pfs25, *P. faciparum* Pfs28, *P. faciparum* PFS27/25, *P. faciparum* Pfs16, *P. faciparum* Pfs48/45, *P. faciparum* Pfs230, and any analogues of *P. faciparum* antigens from *Plasmodium* ssp.

\* \* \* \* \*

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: CpG immunostimulatory oligonucleotide

<400> SEQUENCE: 1
tccatgagct tcctgacgtt                                               20

<210> SEQ ID NO 2
<211> LENGTH: 18
<212> TYPE: DNA
<213> ORGANISM: Artificial Sequence
<220> FEATURE:
<223> OTHER INFORMATION: CpG immunostimulatory oligonucleotide

<400> SEQUENCE: 2
tctcccagcg tgcgccat                                                 18

<210> SEQ ID NO 3
<211> LENGTH: 24
<212> TYPE: DNA
<213> ORGANISM: Artificial Sequence
<220> FEATURE:
<223> OTHER INFORMATION: CpG immunostimulatory oligonucleotide

<400> SEQUENCE: 3
tcgtcgtttt gtcgttttgt cgtt                                          24